United States Patent [19]

Tsunemi et al.

[11] Patent Number: 5,360,887
[45] Date of Patent: Nov. 1, 1994

[54] FLAME-RETARDED THERMOSETTING RESIN COMPOSITION, PREPREGS AND ELECTRICAL LAMINATES MADE THEREFROM

[75] Inventors: Hidenari Tsunemi, Takashima; Toshinobu Nakata; Koyoyuki Namura, both of Otsu, all of Japan

[73] Assignee: Kanegafuchi Kagaku Kogyo Kabushiki Kaisha, Osaka, Japan

[21] Appl. No.: 98,087

[22] Filed: Jul. 28, 1993

[30] Foreign Application Priority Data

Jul. 29, 1992 [JP] Japan .................................. 4-223499
Jul. 29, 1992 [JP] Japan .................................. 4-223502
Aug. 26, 1992 [JP] Japan .................................. 4-252087

[51] Int. Cl.$^5$ ............................................. C08G 83/00
[52] U.S. Cl. ........................................ 528/97; 528/99; 528/119; 528/120; 528/271; 528/363; 528/422; 560/301; 558/418; 558/419; 558/420; 558/421; 428/209; 428/422.8; 428/457; 428/901
[58] Field of Search ............... 528/67, 97, 99, 119, 528/120, 271, 363, 422; 428/209, 422.8, 457, 901, 209; 568/301; 560/301; 558/418, 419, 420, 421

[56] References Cited

U.S. PATENT DOCUMENTS

| | | | |
|---|---|---|---|
| 4,097,455 | 6/1978 | Burkhardt et al. | 528/67 |
| 4,996,267 | 2/1991 | Gerth et al. | 525/423 |
| 5,045,381 | 9/1991 | Suzuki et al. | 428/309 |
| 5,089,660 | 2/1992 | Murray et al. | 560/301 |
| 5,276,106 | 1/1994 | Portelli | 525/423 |

OTHER PUBLICATIONS

Papathomas et al., "Triazine Networks Modified with Monofunctional Reactive . . . ". J. of App. Poly. Sci., vol. 44, No. 7, pp. 1267–1274.

IBM Technical Disclosure Bull, vol. 26, No. 7B, Dec. 1983, p. 3773.

*Primary Examiner*—John Kight, III
*Assistant Examiner*—Duc Truong
*Attorney, Agent, or Firm*—Millen, White, Zelano, & Branigan

[57] ABSTRACT

A flame-retarded thermosetting resin composition is provided by blending about 5 to 45 mole % of a phenylcyanate having at least one halogen substituent at the ortho or para position relative to the cyanato group, and about 55 to 95 mole % of a halogen-free bis-4-phenylcyanate. A flame retardancy of V-O grade of UL94 is achieved in the thermoset resin of the composition without compromising dielectric, heat resistance, moisture absorption and other properties.

16 Claims, No Drawings

FLAME-RETARDED THERMOSETTING RESIN COMPOSITION, PREPREGS AND ELECTRICAL LAMINATES MADE THEREFROM

BACKGROUND OF THE INVENTION

This invention relates to a novel flame-retarded thermosetting resin composition for use in the manufacture of various electric and electronic parts such as electrical laminates and prepregs that require excellent dielectric and flame-retardant characteristics. The resin composition of this invention is also useful for bonding, coating, casting, potting and molding purposes where such characteristics are required in the thermoset resin used in electric and electronic parts. The term "electrical laminates" as used herein refers to unclad insulation boards for mounting various parts thereon, as well as metal clad laminates for use in the manufacture of printed circuit boards.

Recently, frequencies used in electronic communication equipment, computers and the like are reaching a high frequency region such as the megahertz (MHz) or gigahertz (GHz) regions. Insulation materials used in such high frequency regions are required to have a low dielectric loss tangent as well as a low dielectric constant. To this end, a variety of resins having a low dielectric constant and low dielectric loss tangent have been developed. Among them, cyanate ester resins are excellent in these dielectric properties. Bisphenol A dicyanate ester resins, for example, have been used in fabricating electrical laminates, while Japanese Laid Open Patent Application No. 250359/1988 discloses a fluorine-containing dicyanate ester for producing thermosetting resins having excellent dielectric properties.

Electrical laminates often require a flame retardancy of V-O in the UL94 standard. The prior art dicyanate ester resins, including just mentioned resins, have excellent dielectric properties compared to epoxy, polyester, phenol and polyimide resins which are conventionally used in the manufacture of electrical laminates. However, their dielectric loss tangent is not fully satisfactory in high frequency regions particularly in the GHz region. Cyanate ester resins with a flame retardant additive having a flame retardancy of V-O in the UL94 standard generally have a dielectric loss tangent greater than that of the corresponding non-flame retarded dicyanate ester resins and, therefore, they are not suitable as matrix resins of electrical laminates used in the GHz telecommunication field. The fluorine-containing dicyanate esters disclosed in Japanese Laid Open Patent Application No. 250359/1988 may provide resins having a flame retardancy of V-O but they are too expensive for practical applications. It is desirable for electrical laminates used in the telecommunication field to have a dielectric loss tangent less than 0.005 and preferably less than 0.004. It is also desirable for the matrix resin of such laminates to have a dielectric loss tangent less than 0.006, and preferably less than 0.005 in the GHz region. For computer applications, the electrical laminates should desirably have a dielectric constant less than 4.0 in the GHz region to enable faster operation. These laminates are often composed of glass cloth substrates of E glass. In this case, the matrix resin should desirably have a dielectric constant less than 3.0, and more preferably less than 2.9.

Moisture absortion is an important factor which adversely affects the dielectric properties in the high frequency region, and in the GHz region in particular. The prior art dicyanate ester resins tend to have relatively high moisture adsorption.

Also required for the matrix resin of electrical laminates are good heat stability and a high glass transition temperature (Tg). These characteristics are important for the dimensional stability and reliability of printed circuit boards (PCB's) made therefrom. For use as multilayer PCB's, the matrix resin should have a Tg of higher than 160° C., preferably higher than 170° C., and most preferably higher than 180° C., measured by the TMA method. Resins having a low dielectric loss tangent in the GHz region and a high Tg are not yet known.

It is, therefore, an object of this invention to provide a thermosetting cyanate ester resin composition having a low dielectric constant and a low dielectric loss tangent in the GHz region in particular, as well as a satisfactory flame retardancy, a low moisture absorption and a high Tg. It is another object of the present invention to provide an electrical laminate and prepregs therefor having excellent dielectric characteristics in the GHz region as well as a low moisture absorption and a satisfactory flame retardancy. Other objects and advantages of the present invention will become apparent as the description proceeds.

SUMMARY OF THE INVENTION

The above and other objects are accomplished by the present invention. In accordance with the present invention, there is provided a flame-retarded thermosetting resin composition comprising:

(a) about 5 to about 45 mole % of an aromatic monocyanate ester of the formula I:

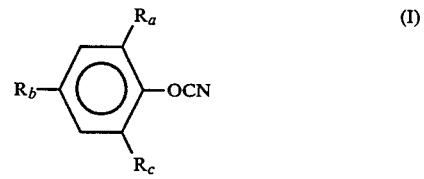

wherein $R_a$, $R_b$ and $R_c$ are same or different and each is hydrogen, alkyl, aryl or halogen, at least one of $R_a$, $R_b$ and $R_c$ being halogen; and (b) about 55 to about 95 mole % of a dicyanate ester of the formula II;

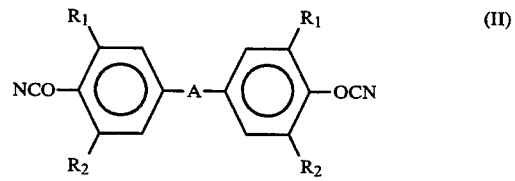

wherein $R_1$ and $R_2$ are same or different and each is hydrogen, alkyl or aryl, and A is a bridge selected from the group consisting of direct bond, methylene, mono- or disubstituted methylene with alkyl and/or aryl, a five or six membered cycloalkylene, sulfonyl, thio, oxy, carbonyl, xylylene optionally substituted by alkyl at one or both methylene carbon atoms and phenylene.

The present invention also provides prepolymers produced by reacting the above blend of mono- and dicyanate esters monomers, prepregs impregnated with said prepolymers, and electrical laminates made by combining several sheets of the prepregs with cladding metal under heat and pressure.

The term "cyanate ester" as used herein refers to monomeric cyanate esters, while the term "prepolymer" refers to a reaction mixture in which some or all monomeric cyanate esters have been converted to oligomers such as trimers. Specifically, these prepolymers include such oligomers and mixtures of oligomers with monomers. Preferably, the conversion rate T is within the range of $0\% < T < 60\%$.

Using the above resin composition, it is possible to produce flame retarded single or multilayered PCB's having a low dielectric constant and dielectric loss tangent in the GHz region as well as various resin products for bonding, coating, potting or casting purposes where similar dielectric characteristics are desired.

DETAILED DISCUSSION

The dicyanate ester used in the present invention must be of the above formula II, namely of bis(4-cyanatophenyl) type. In our Japanese Patent Application No. 75148/1992, a cured product from bis(2-cyanatophenyl) type monomers is disclosed having a low dielectric loss tangent in the GHz region. However, it was found that when this type of dicyanate ester is blended with a halogen-containing monocyanate ester to impart sufficient flame retardancy, the resulting cured product often exhibited a compromised dielectric loss tangent compared with the cured product of the dicyanate ester alone. Surprisingly, we have found that when halogen-free bis(4-cyanatophenyl) type dicyanate esters are blended with the halogen-containing monocyanate ester, a cured resin may be obtained with satisfactory flame retardancy as well as a significantly lower dielectric loss tangent than when curing the halogen-free dicyanate ester alone.

Halogen-free dicyanate esters of the Formula II may be produced from the corresponding 4,4'-bisphenols. These bisphenols are readily and cheaply available making the resin composition cost effective.

$R_1$ and R2 are the same or different and each is hydrogen, alkyl or aryl. Examples of alkyls are $C_1$-$C_5$ alkyl such as methyl, ethyl, n-propyl, isopropyl, n-butyl, isobutyl, t-butyl or isomeric pentyl, of which methyl, ethyl, isopropyl and t-butyl are particularly preferred. Examples of aryl include phenyl, mono- or disubstituted phenyl with a $C_1$-$C_4$ alkyl such as o-, m-, or p-tolyl, 1- or 2-naphthyl, and a $C_1$-$C_4$ alkyl-monosubstituted naphthyl. Here, phenyl and mono- or disubstituted phenyl with a $C_1$-$C_4$ alkyl, and particularly phenyl and tolyl are preferable.

The bridge A may be a direct bond, methylene or mono- or di-substituted methylene with alkyl, and/or aryl such as 1,1-ethylidene, 1,1-propylidene, 2,2-propylidene, 3,3-pentylidene, mono- or diphenylmethylene, methylphenylmethylene, ethylphenylmethylene and the like. The bridge A may also be a five or six membered cycloalkylene such as cyclopentylene or cyclohexylene, sulfonyl namely —$SO_2$—, thio namely —S—, oxy namely —O—, carbonyl namely —CO—, or xylylene optionally substituted by a $C_1$-$C_2$ alkyl at one or both methylene carbon atoms. The term "xylylene" refers to 1,2-, 1,3 or 1,4-benzene-bismethylene bridge. Tetramethylxylylene is a typical example of a methylene-alkylated xylylene. Dicyanate esters of bisphenol A, tetramethylbisphenol F and bisphenol C, respectively, are particularly preferable for reasons of availability and cost.

The resin composition of the present invention contains a halogen-containing aromatic monocyanate ester of the formula I, where $R_a$, $R_b$ and $R_c$ are same or different and each is hydrogen, alkyl, aryl or halogen. At least one, and preferably at least two of $R_a$, $R_b$ and $R_c$ must be halogen. Examples of alkyls are a $C_1$-$C_5$ alkyl such as methyl, ethyl, n-propyl, isopropyl, n-butyl, isobutyl, t-butyl or isomeric pentyl, of which methyl, ethyl, isopropyl and t-butyl are particularly preferred. Examples of aryl include phenyl, mono- or disubstituted phenyl with a $C_1$-$C_4$ alkyl such as o-, m- or p-tolyl, 1- or 2-naphthyl, and a $C_1$-$C_4$ alkyl-monosubstituted naphthyl. Here, phenyl and mono- or disubstituted phenyl with a $C_1$-$C_4$ alkyl, particularly phenyl and tolyl are preferred. Preferably, the halogen is bromine or chlorine. Specifically, monocyanate esters of 2,4- or 2,6-dibromophenol, 2,4,6-tribromophenol, 2,4-dibromo-6-methylphenol and 2,6-dibromo-4-methylphenol, respectively, and mixtures thereof are preferred examples of the monocyanate esters of the formula I.

WO 89/04823 discloses a monofunctional phenylcyanate having an alkyl or substituted methyl at each ortho position relative to the cyanato group and at least one halogen at the remaining position. This monofunctional cyanate is blended with a monomeric polycyanate having a recurring unit of cyclopentadiene/phenylcyanate adduct to improve the toughness of the resulting polytriazine resin. Although the mechanical properties are the main concern of this reference, polycyanurate resins are in general inherently stronger than, for example, epoxy resins and, therefore, further improvement in mechanical properties will hardly be required for PCB applications. If the mechanical properties are compromised by blending a monocyanate ester, the presence of reinforcing substrates in the PCB's will compensate for the compromised mechanical properties. Accordingly, improvements in the dielectric constant, dielectric loss tangent, moisture absorption, manufacturing cost and other advantages achieved by the present invention are more significant for PCB or similar applications.

The above monocyanate ester of the formula I and the dicyanate ester of the formula II may be produced by reacting the corresponding phenol with a cyanogen halide in the presence of an acid acceptor such as triethylamine. The reaction is known per se as is disclosed, for example, U.S. Pat. No. 3,553,244 of which the entire disclosure is incorporated herein by reference. For example, to a stoichiometric mixture of a phenol and cyanogen bromide in acetone is added dropwise an amount of triethylamine at a temperature between 0° C. and 10° C. with stirring. After removing the resulting triethylamine hydrobromide, the cyanate ester may be isolated from the reaction mixture by any conventional method.

In use, the resin composition of the present invention may be intermixed, or blended with less than 20, preferably 10 weight % of a conventional thermosetting resin such as epoxy, polyester, epoxy-acrylate, urethane-acrylate, diallyl phthalate, spiropyrane, phenol, polyimide or like resins, or a conventional thermoplastic resin such as fluororesin, polyphenyleneoxide, polyphenylenesulfide or polycarbonate resin. The composition may also contain a curing catalyst such as imidazole compounds, tertiary amines or organometallic compounds. Organometallic compounds such as cobalt octanate, zinc octanate, cobalt naphthenate or zinc naphthenate are preferable. The curing reaction may be accelerated by the addition of a small amount of phenols such as bisphenol A, bisphenol F, bisphenol S or p-nonylphenol. The composition may contain a filler such as alumina, aluminum hydroxide, antimony tri- or pentoxide, zinc oxide, titanium dioxide, silica powder, quartz powder, glass powder, ceramic microballoons, or mixtures thereof.

For casting applications, the cyanate ester composition is heated to a molten state to produce a prepolymer composition before casting into a mold, and then allowed to cure at an elevated temperature.

For bonding applications, a resin varnish or molten prepolymer composition may be applied on the surfaces to be bonded, and then allowed to cure under heat and pressure.

Prepregs are produced by impregnating a suitable substrate with a resin varnish produced from the composition of the present invention. The resin varnished is prepared by blending about 5 to 45 mole % of the halogen-containing monocyanate ester of the formula I and about 55 to 95 mole % of the dicyanate ester of the formula II, and heating the blend to produce a prepolymer composition. Alternatively, a prepolymer of the dicyanate ester of the formula II in an amount corresponding to said mole % of the monomeric dicyanate ester may be reacted with the monomeric monocyanate. When blending the mono- and dicyanate esters, a proportion of monocyanate ester of greater than 45 mole % compromises the mechanical strength and heat resistance of the finished laminates. Conversely, a proportion of monocyanate ester less of than 5 mole % has little effect on the improvement in dielectric and other properties. In order to improve dielectric, moisture absorbing, flame-retarding and other properties, a blend consisting of 7–40 mole %, preferably 10–35 mole % of the monocyanate ester and the balance of the dicyanate ester or its prepolymer is desirable. Most desirably, the proportion of monocyanate ester is optimized within the above range while taking the halogen content of individual monocyanate esters into account. In other words, the halogen content of the blend is desirably adjusted to obtain a good balance between the dielectric, moisture absorption, heat resistant (Tg) properties and the flame retardancy grade of V-O. The bromine content in the matrix resin ranges preferably from 4 to 30% by weight, and more preferably from 6 to 25% by weight. On the other hand, a significant improvement in dielectric loss tangent and moisture absorption may be expected by blending the monocyanate in a proportion from 7 to 40 mole %. The bromine content may be adjusted by using high-to-low bromine containing monocyanates such as 2,4,6-tribromophenyl cyanate, 2,4-dibromophenyl-cyanate, p-bromophenylcyanate individually or in combination. Excessive bromine contents will compromise the long term heat resistance and thermal decomposition temperature and, therefore, should be avoided for electrical laminates, coating and casting applications.

The prepolymer produced from a blend of mono- and dicyanate esters is made into a varnish by dissolving in a volatile organic solvent. Examples of solvents include ketones such as acetone, methyl ethyl ketone or methyl isobutyl ketone; aromatic hydrocarbons such as toluene or xylene; ethers such as dioxane, tetrahydrofuran or ethylene glycol monomethyl ether; alcohols such as methanol, ethanol or isopropyl alcohol; amides such as dimethylformamide or dimethylacetamide; and mixtures of these solvents. Aromatic hydrocarbons and ketones such as acetone or methyl ethyl ketone are suitable. The varnish may contain a catalyst and/or phenol as described above as well as fillers.

Prepregs may be produced by impregnating a continuous length of a substrate with a resin varnish and drying the impregnated substrate. The impregnation apparatus may be of conventional design but a vertical type is preferable. Alternatively, the substrate may be impregnated with a molten prepolymer produced from the composition of this invention. Examples of substrates used in the preparation of prepregs include glass fiber substrates such as glass cloth or glass nonwoven fabric, cellulosic substrates such as kraft paper or cotton linter paper, synthetic fiber fabric such as aramide cloth or aramide nonwoven fabric. Composite laminates may be produced using different types of substrate in combination. The glass material may be E glass, D glass, S glass, T glass or quartz glass.

The production of electrical laminates may be batchwise or continuous. In the batchwise process, a plurality of prepregs of a predetermined size are stacked with a cladding metal foil being placed on one or both sides, and compressed between a pair of hot plates of a press under heat and pressure. In the continuous process, a continuous length of prepreg rolled in a coil is prepared. A plurality of prepregs are paid down from their coils, led into a continuous press, such as a double belt press, along with the cladding metal foil, and then compressed in the press under heat and pressure. Alternatively, the laminate may be produced continuously by paying down a plurality of substrates, impregnating the plurality of substrates with a molten liquid of the dicyanate ester or prepolymer, joining the impregnated substrates into a laminate, applying a cladding metal foil on one or both sides, and then curing the laminate without applying pressure.

The following examples are intended to further illustrate the invention without limiting it thereto. All parts and percents therein are by weight unless otherwise indicated.

In the following Examples, various properties were determined according to the following methods.

Dielectric Properties

Measurements of dielectric constant and dielectric loss tangent were made by the perturbation principle using a network analyzer (Model HP8410B) and a rectangular cavity resonator having a resonant frequency of about 2.5 GHz sold by SHIMADA RIKA K.K.

Moisture Absorption

Specimens were made by removing copper foils from laminates of 5×5 cm size by etching, treated in a box kept at a constant temperature of 40° C. and a relative humidity of 90% for 96 hours, and then the moisture absorption measured.

Glass Transition Temperature

Tg was determined by TMA at a heating rate of 10° C./minute.

EXAMPLE 1

2,4-dibromophenylcyanate (DBP-CY)

A three necked flask equipped with a drip funnel, thermometer and stirrer was charged with a solution of 58.3g of cyanogen bromide in 200 ml of isopropanol, purged with nitrogen gas, and cooled to between −5°

C. and +3° C. A solution of 126 g of 2,4-dibromophenol and 53.1 g of triethylamine in 300 ml of isopropanol was added dropwise from the drip funnel with stirring at a drip rate sufficient to maintain the inner temperature at below 10° C. After the addition, the reaction mixture was stirred at a temperature below 10° C. for 2 hours. The resulting white precipitate was filtered off, washed thoroughly with a large amount of water, and dried in vacuo. 83.1 g (60% of theory) of the title compound was obtained as white crystals. The product was identified to be the title compound by its NMR spectrum as well as by the absorption of the cyanato group at 2270 cm$^{-1}$ in its IR spectrum.

EXAMPLE 2

Dibromomethylphenylcyanate (DBC-CY)

Analogous to Example 1, commercial dibromocresol(mixture of isomors sold by MANAC K.K. under the name of DBC) was reacted with cyanogen bromide. The title compound was obtained as white crystals in a yield of 60% of theory. The product was identified by its NMR spectrum as well as by the absorption of the cyanato group at 2260 cm$^{-1}$ and the absence of phenolic hydroxy absorption in the IR spectrum.

EXAMPLE 3

4-bromophenylcyanate (PBP-CY)

Analogous to Example 1, p-bromophenol was reacted with cyanogen bromide to obtain the title compound as white crystals. The yield was 63% of theory. The product was identified by its NMR spectrum as well as by the absorption of the cyanato group at 2260 cm$^{-1}$ and the absence of phenolic hydroxy absorption in the IR spectrum.

EXAMPLE 4

2,4,6-tribromophenylcyanate (TBP-CY)

Analogous to Example 1, 2,4,6-tribromophenol was reacted with cyanogen bromide to obtain the title compound as white crystals. The yield was 60% of theory. The product was identified by elementary analysis and its NMR spectrum as well as by the absorption of the cyanato group at 2270 cm$^{-1}$ in the IR spectrum.

EXAMPLE 5

2,2-bis(4-cyanatophenyl)propane(BIS A-CY)

A three necked flask equipped with a drip funnel, thermometer and stirrer was charged with 46.6 g of cyanogen bromide and 45.7 g of 2,2-bis(4-hydroxyphenyl)propane in 300 ml of acetone and cooled to a temperature of between −5° C. and +3°C. To the solution was added dropwise 43.5 g of triethylamine with stirring at a rate sufficient to maintain the inner temperature below 10° C. After the addition, the reaction mixture was stirred for an additional 2 hours at 10° C. and then filtered to remove white precipitates. The filtrate was poured into a large volume of water whereupon white crystals were precipitated. These crystals were recrystalized from ethanol to give 43.2 g (78% of theory) of the title compound. The product was identified by its NMR spectrum as well as by the absorption of the cyanato group at 2260 cm$^{-1}$ in its IR spectrum.

EXAMPLES 6-8

Resin compositions

DBP-CY, DBC-CY or PBP-CY was blended with BIS A-CY at a weight ratio of 3:7 and heated at 150° C. for a length of time sufficient to achieve 10–40% conversion of the monomeric cyanates into prepolymers. The resulting prepolymer was cast into a Teflon mold and cured at 200° C. for 1–5 hours and then at 250° C. for 3 hours, to produce a specimen having 5 mm thickness. This specimen was machined into a rectangular rod of 4×4×100 mm size, and its dielectric characteristics, moisture absorption, Tg and flame retardancy were determined. The conversion rate of cyanato groups in the fully cured product was greater than 99%. The results obtained are shown in Table 1.

TABLE 1

| Item | Ex. 6 | Ex. 7 | Ex. 8 |
|---|---|---|---|
| Monocyanate | DBP-CY | DBC-CY | PBP-CY |
| Dielectric constant | 2.80 | 2.78 | 2.79 |
| Dielectric loss tangent | 0.0027 | 0.0033 | 0.0032 |
| Tg, °C. | 203 | 208 | 190 |
| Moisture absorption | 0.73 | 0.70 | 0.71 |
|  | 1 8 |  |  |
| Flame retardancy in UL 94 | V-O | V-O | V-O |

EXAMPLES 9-14 AND COMPARATIVE EXAMPLES 1-2

Resin Compositions

TBY-CY and BIS A-CY were blended in the proportions shown in Table 2, and heated in an oven at 150° C. for 2 hours to convert the monomeric cyanate blend to a prepolymer. Thereafter the prepolymer was cast into a Teflon mold, cured at 200° C. for 2 hours, and then post cured at 250° C. for 3 hours after removing it from the mold.

Using specimens of the cured resins of Examples 9-14 and Comparative Examples 1-2, the dielectric constant, dielectric loss tangent, Tg, moisture absorption and flame retardancy were determined. The results are shown in Table 2. As shown in the table, the products of Examples were excellent in all items compared to the product of Comparative Examples.

TABLE 2

|  | Examples | | | | | | Comparative EX. | |
|---|---|---|---|---|---|---|---|---|
|  | 9 | 10 | 11 | 12 | 13 | 14 | 1 | 2 |
| TBP-CY, mole % | 12 | 25 | 30 | 35 | 40 | 45 | 0 | 50 |
| BIS A-CY, mole % | 88 | 75 | 70 | 65 | 60 | 55 | 100 | 50 |
| Dielectric constant (2.5 GHz) | 2.81 | 2.80 | 2.81 | 2.84 | 2.86 | 2.88 | 2.84 | 2.90 |
| Dielectric loss tangent (2.5 GHz) | 0.0047 | 0.0035 | 0.0035 | 0.0035 | 0.0035 | 0.0039 | 0.0069 | 0.0058 |
| Tg, °C. | 235 | 219 | 210 | 185 | 178 | 165 | 237 | 145 |
| Moisture absorption, % | 0.80 | 0.71 | 0.65 | 0.70 | 0.71 | 0.78 | 1.42 | 1.50 |
| Ul 94 | V-O | V-O | V-O | V-O | V-O | V-O | HB | V-O |

EXAMPLE 15

2,2-bis(3,5-dimethyl-4-cyanatophenyl)propane(TM BIS A-CY)

Analogous to Example 5, 2,2-bis(3,5-dimethyl-4-hydroxyphenyl)propane was reacted with cyanogen bromide to obtain white crystals of the title compound. The yield was 75% after recrystallization from ethanol. The product was identified by its NMR and elementary analysis as well as by the absorption of the isocyanato group at 2260 cm$^{-1}$ in its IR spectrum.

EXAMPLES 16–19 AND COMPARATIVE EXAMPLES 3–4

Resin compositions

TBP-CY and TM BIS -CY were blended in the proportions shown in Table 3, and heated in an oven at 150° C. for 2 hours to convert the monomeric cyanate blend to a prepolymer. Thereafter the prepolymer was cast into a Teflon mold, cured at 200° C. for 2 hours, and then post cured at 250° C. for 3 hours after removing it from the mold.

Using specimens of the cured resins of Examples 16–19 and Comparative Examples 3–4, the dielectric constant, dielectric loss tangent, Tg, moisture absorption and flame retardancy were determined. The results are shown in Table 3. As shown in the table, the products of Examples were excellent in all items compared to the products of Comparative Examples.

TABLE 3

|  | Examples | | | | Comparative EX. | |
|---|---|---|---|---|---|---|
|  | 16 | 17 | 18 | 19 | 3 | 4 |
| TBP-CY, mole % | 15 | 20 | 30 | 40 | 0 | 50 |
| TM BIS A-CY, mole % | 85 | 80 | 70 | 60 | 100 | 50 |
| Dielectric constant (2.5 GHz) | 2.65 | 2.63 | 2.64 | 2.70 | 2.66 | 2.75 |
| Dielectric loss tangent (2.5 GHz) | 0.0042 | 0.0036 | 0.0036 | 0.0040 | 0.0070 | 0.0073 |
| Tg, °C. | 223 | 218 | 202 | 178 | 238 | 147 |
| Moisture absorption, % | 0.71 | 0.65 | 0.59 | 0.68 | 1.40 | 1.38 |
| Ul 94 | V-O | V-O | V-O | V-O | HB | V-O |

EXAMPLES 20–23 AND COMPARATIVE EXAMPLE 5

Resin Compositions

DBP-CY and BIS A-CY were blended in the proportions shown in Table 4, and heated in a oven at 150° C. for 2 hours to produce a prepolymer. Thereafter the prepolymer was cast into a Teflon mold, cured at 200° C. for 2 hours, and then post cured at 250° C. for 3 hours after removing it from the mold.

Using specimens of the cured resins of Examples 20–23 and Comparative Example 5, the dielectric constant, dielectric loss tangent, Tg, moisture absorption and flame retardancy were determined. The results are shown in Table 4. As shown in the table, the products of Examples were excellent in all items compared to the products of Comparative Examples.

TABLE 4

|  | Examples | | | | Comparative EX. | |
|---|---|---|---|---|---|---|
|  | 20 | 21 | 22 | 23 | 1 | 5 |
| DBP-CY, mole % | 15 | 20 | 30 | 40 | 0 | 50 |
| BIS A-CY, mole % | 85 | 80 | 70 | 60 | 100 | 50 |
| Dielectric constant (2.5 GHz) | 2.82 | 2.82 | 2.80 | 2.82 | 2.84 | 2.80 |
| Dielectric loss tangent (2.5 GHz) | 0045 | 0.0035 | 0.0027 | 0.0022 | 0.0069 | 0.0019 |
| Tg, °C. | 220 | 212 | 203 | 175 | 237 | 138 |
| Moisture absorption, % | 0.79 | 0.65 | 0.60 | 0.57 | 1.42 | 0.82 |
| UL 94 | V-O | V-O | V-O | V-O | HB | V-O |

EXAMPLES 24–29 AND COMPARATIVE EXAMPLES 6–7

Prepregs and Laminates

A blend of TBP-CY and BIS A-CY in the proportion shown in Table 5 was heated at 150° C. for 3 hours to produce a prepolymer having 40% conversion of the cyanate groups. A varnish was prepared by dissolving the prepolymer in methyl ethyl ketone (MEK) to give a nonvolatile content of 65%. To the varnish were added 0.03 parts of zinc octanate and 1.3 parts of bisphenol A per 100 parts of the varnish.

A 7628 type E glass cloth of 180 μm thickness was impregnated with the above varnish and dried, to obtain a prepreg having a resin content of about 50%. Seven sheets of the prepreg were stacked and a pair of copper foils of 18 μm thickness each were placed on both sides of the stack. This assemblage was compression molded in a press for 90 minutes under a molding pressure of 20–30 kg/cm² at 170° C. and subjected to post curing at 220° C. for 2 hours. A double sided copper laminate of 1.6 mm thickness was produced.

The resulting laminates were tested for dielectric constant, dielectric loss tangent, Tg and moisture absorption. The results are shown in Table 5. As shown in the Table, the laminates of Examples were excellent in all items compared to the laminates of Comparative Examples.

TABLE 5

|  | Examples | | | | | | Comparative EX. | |
|---|---|---|---|---|---|---|---|---|
|  | 24 | 25 | 26 | 27 | 28 | 29 | 6 | 7 |
| TBP-CY, mole % | 12 | 25 | 30 | 35 | 40 | 45 | 0 | 50 |

TABLE 5-continued

|  | Examples | | | | | | Comparative EX. | |
| --- | --- | --- | --- | --- | --- | --- | --- | --- |
|  | 24 | 25 | 26 | 27 | 28 | 29 | 6 | 7 |
| BIS A-CY, mole % | 88 | 75 | 70 | 65 | 60 | 55 | 100 | 50 |
| Dielectric constant (2.5 GHz) | 4.0 | 3.9 | 3.9 | 4.0 | 4.0 | 4.1 | 4.0 | 4.1 |
| Dielectric loss tangent (2.5 GHz) | 0.0042 | 0.0038 | 0.0038 | 0.0044 | 0.0043 | 0.0048 | 0.0073 | 0.0068 |
| Tg, °C. | 235 | 205 | 195 | 180 | 170 | 165 | 237 | 140 |
| Moisture absorption, % | 0.30 | 0.23 | 0.23 | 0.32 | 0.33 | 0.35 | 0.55 | 0.63 |
| UL 94 | V-O | V-O | V-O | V-O | V-O | V-O | HB | V-O |

EXAMPLES 30–33 AND COMPARATIVE EXAMPLES 8–9

Prepregs and Laminates

Analogous to Examples 24–29, double sided copper clad laminates of 1.6 mm thickness were produced from blends of TBP-CY and TM BIS A-CY having the proportion shown in Table 6, and tested for their dielectric constant, dielectric loss tangent, Tg and moisture absorption. The results are shown in Table 6. As shown in the table, the laminates of Examples were excellent in all items compared to the laminates of Comparative Examples.

TABLE 6

|  | Examples | | | | Comparative EX. | |
| --- | --- | --- | --- | --- | --- | --- |
|  | 30 | 31 | 32 | 33 | 8 | 9 |
| TBP-CY, mole % | 15 | 20 | 30 | 40 | 0 | 50 |
| TM BIS A-CY, mole % | 85 | 80 | 70 | 60 | 100 | 50 |
| Dielectric constant (2.5 GHz) | 3.8 | 3.8 | 3.8 | 3.9 | 3.9 | 4.0 |
| Dielectric loss tangent (2.5 GHz) | 0.0040 | 0.0039 | 0.0035 | 0.0040 | 0.0072 | 0.0073 |
| Tg, °C. | 223 | 215 | 201 | 175 | 238 | 140 |
| Moisture absorption, % | 0.29 | 0.24 | 0.21 | 0.27 | 0.50 | 0.59 |
| UL 94 | V-O | V-O | V-O | V-O | HB | V-O |

EXAMPLES 34–37 AND COMPARATIVE EXAMPLE 10

Prepregs and Laminates

Analogous to Examples 24–29, double sided copper clad laminates of 1.6 mm thickness were produced from blends of DBP-CY and BIS A-CY having the proportions shown in Table 7, and tested for their dielectric constant, dielectric loss tangent, Tg and moisture absorption. The results are shown in Table 7. As shown in the table, the laminates of Examples were excellent in all important items compared to the laminates of Comparative Examples.

TABLE 7

|  | Examples | | | | Comparative EX. | |
| --- | --- | --- | --- | --- | --- | --- |
|  | 34 | 35 | 36 | 37 | 6 | 10 |
| DBP-CY, mole % | 15 | 20 | 30 | 40 | 0 | 50 |
| BIS A-CY, mole % | 85 | 80 | 70 | 60 | 100 | 50 |
| Dielectric constant (2.5 GHz) | 4.0 | 3.9 | 3.9 | 4.0 | 4.0 | 4.1 |
| Dielectric loss tangent (2.5 GHz) | 0.0043 | 0.0039 | 0.0035 | 0.0033 | 0.0073 | 0.0032 |
| Tg, °C. | 218 | 209 | 197 | 170 | 237 | 133 |
| Moisture absorption, % | 0.29 | 0.23 | 0.18 | 0.19 | 0.55 | 0.33 |
| UL 94 | V-O | V-O | V-O | V-O | HB | V-O |

What is claimed is:

1. A flame-retarded thermosetting resin composition comprising:

(a) about 5 to about 45 mole % of an aromatic monocyanate of the formula I:

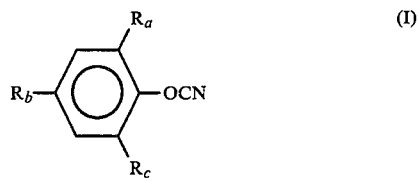

wherein $R_a$ is hydrogen, and $R_b$ and $R_c$ are alkyl, aryl or halogen, where at least one of $R_b$ and $R_c$ is halogen; and (b) about 55 to about 95 mole % of a dicyanate of the formula II:

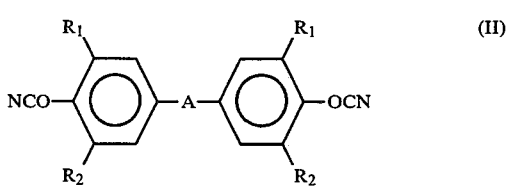

wherein $R_1$ and $R_2$ are same or different and each is hydrogen, alkyl or aryl, and A is a bridge selected from the group consisting of a direct bond, methylene, methylene mono- or disubstituted with alkyl and/or aryl, a five or six membered cycloalkylene, sulfonyl, thio, oxy, carbonyl, xylylene optionally substituted by alkyl at one or both methylene carbon atoms and phenylene.

2. The flame-retarded thermosetting resin composition of claim 1, wherein said aromatic monocyanate is 2-alkyl-4-bromophenylcyanate, a 4-alkyl-2-bromophenylcyanate or 2,4-dibromophenylcyanate.

3. The flame retarded thermosetting resin composition of claim 1, wherein said dicyanate is 2,2-bis(4-cyanatophenyl) propane, 2,2-bis(3,5-dimethyl-4-cyanatophenyl)propane or bis(3,5-dimethyl-4-cyanatophenyl)methane.

4. A prepreg made of a fibrous substrate impregnated with a prepolymer of the resin composition of claim 1.

5. A prepreg made of a fibrous substrate impregnated with a prepolymer of the resin composition of claim 2.

6. A prepreg made of a fibrous substrate impregnated with a prepolymer of the resin composition of claim 3.

7. An electrical laminate comprising a plurality of prepregs of claim 4.

8. The electrical laminate of claim 7 further comprising a cladding metal foil applied on one or both sides thereof.

9. An electrical laminate comprising a plurality of prepregs of claim 5.

10. The electrical laminate of claim 9 further comprising a cladding metal foil applied on one or both sides thereof.

11. An electrical laminate comprising a plurality of prepregs of claim 6.

12. The electrical laminate of claim 11 further comprising a cladding metal foil applied on one or both sides thereof.

13. A compound of the formula I:

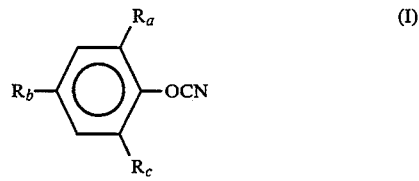

wherein $R_a$ is hydrogen, and $R_b$ and $R_c$ are alkyl, aryl or halogen, at least one of $R_b$ and $R_c$ being halogen.

14. The compound of claim 13, which is a 2-alkyl-4-bromophenylcyanate, a 4-alkyl-2bromophenylcyanate or 2,4-dibromophenylcyanate.

15. The flame-retarded thermosetting resin composition of claim 1, wherein said aromatic monocyanate is 2-methyl-4-bromophenylcyanate or 4-methyl-2-bromophenylcyanate.

16. The compound of claim 13, which is 2-methyl-4-bromophenylcyanate or 4-methyl-2-bromophenylcyanate.

* * * * *